United States Patent [19]

Schawalder

[11] Patent Number: 5,702,479

[45] Date of Patent: Dec. 30, 1997

[54] SHAFT COMPONENT FOR A JOINT ENDOPROSTHESIS

[76] Inventor: Peter Schawalder, Gassackerstrasse 22, CH-3303 Wohlen bei Bern, Switzerland

[21] Appl. No.: 318,866
[22] PCT Filed: Feb. 18, 1994
[86] PCT No.: PCT/CH94/00037
  § 371 Date: Mar. 20, 1995
  § 102(e) Date: Mar. 20, 1995
[87] PCT Pub. No.: WO94/18911
  PCT Pub. Date: Sep. 1, 1994

[30] Foreign Application Priority Data

Feb. 18, 1993 [CH] Switzerland ............ 506/93-5

[51] Int. Cl.$^6$ ............................................ A61F 2/30
[52] U.S. Cl. ................................... 623/23; 623/18
[58] Field of Search .................. 623/18, 19, 22, 623/23

[56] References Cited

U.S. PATENT DOCUMENTS

| | | | |
|---|---|---|---|
| 4,051,559 | 10/1977 | Pifferi | 623/23 |
| 4,384,373 | 5/1983 | Sivash . | |
| 4,908,032 | 3/1990 | Keller | 623/23 |
| 5,002,578 | 3/1991 | Luman . | |
| 5,002,581 | 3/1991 | Paxson et al. | 623/23 |

FOREIGN PATENT DOCUMENTS

| | | | |
|---|---|---|---|
| 0038897 | 11/1981 | European Pat. Off. | 623/23 |
| 0 228 511 | 7/1987 | European Pat. Off. . | |
| 0 295 200 | 12/1988 | European Pat. Off. . | |
| 0 393 608 | 2/1992 | European Pat. Off. . | |
| 2634371 | 1/1980 | France | 623/23 |
| 2 634 371 | 1/1990 | France . | |
| 2685633 | 7/1993 | France | 623/23 |
| 4320086 | 12/1994 | Germany | 623/23 |

Primary Examiner—David Isabella
Attorney, Agent, or Firm—Walter C. Farley

[57] ABSTRACT

The shank unit of a joint endoprosthesis to be implanted in a tubular bone has a hollow, cylindrical, rotationally symmetrical anchoring sub-assembly (2) with a longitudinal axis (1) and an articulating sub-assembly (3). The articulating subassembly (3) is separate and detachably fixed to the anchoring sub-assembly (2). The articulating sub-assembly (3) comprises a rotationally symmetrical base element (31), an axis of rotation (32) and a neck extension (33) mounted eccentrically relative to the base element (31) and subtending an angle α of 70° to the axis of rotation (32) to receive a joint ball (36). The base element of the articulating sub-assembly (3) can be mounted on the anchoring sub-assembly (2) in such a way that its axis of rotation (32) coincides with the longitudinal axis (1) and be detachably fixed to sub-assembly (2) at any angular position relative to the longitudinal axis (1), as a result of which the radial direction of the neck extension (33) is selectively variable to adjust the anterior torsion relative to the anchoring sub-assembly (2).

12 Claims, 2 Drawing Sheets

SHAFT COMPONENT FOR A JOINT ENDOPROSTHESIS

FIELD OF THE INVENTION

The invention concerns a shank unit for an endoprosthesis to be implanted into a tubular bone and including a hollow-cylindrical anchoring sub-assembly with a longitudinal axis and an articulating sub-assembly.

BACKGROUND OF THE INVENTION

A large number of shank units especially for hip-joint protheses are already available, however, they all incur the drawback that the anchoring sub-assembly to be implanted into the bone marrow canal is rigidly joined to its neck part projecting from it and ultimately receiving the joint-ball. Accordingly, once the shank unit has been implanted, it is impossible to adjust the position of the neck relative to the now stationary anchoring sub-assembly. As a result the anterior torsion or the neck-shank angle (centrum collum diaphysary angle CCD) cannot not be adjusted subsequently.

The state of the art suffers from another drawback in that a substantial number of shank units must be kept on hand to meet the main requirements and anatomical particulars (shank diameter, shank length, neck-shank angle, neck length) of a particular patient.

SUMMARY OF THE INVENTION

The object of the invention is to create an easily implanted shank unit allowing changing the neck geometry (anterior torsion, neck-stub angle, neck length, trochanter replacement) during the operation and even after it without the need to remove or fit the already implanted anchoring sub-assembly of the shank unit.

Essentially, the advantages of the invention are the optimal matching of the shank unit to the anatomic particulars and the modular bearing being as compact as possible.

BRIEF DESCRIPTION OF THE DRAWINGS

The invention and further developments are elucidated below by means of an illustrative embodiment of a shank unit for the hip joint. However the invention also applies to shank units of other endoprostheses, illustratively for the shoulder and the fingers.

DESCRIPTION OF THE PREFERRED EMBODIMENTS

Figure 1:
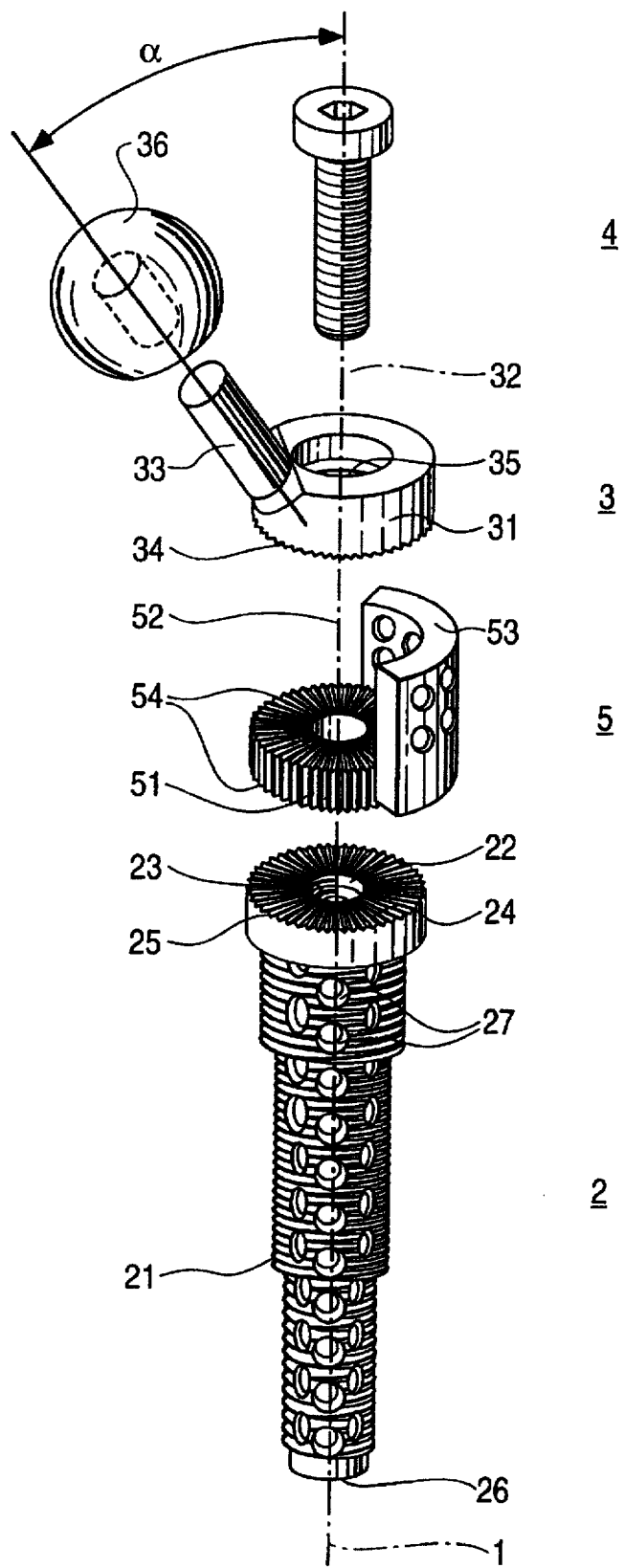
FIG. 1 is an exploded perspective of the shank unit of the invention.
Figure 2:
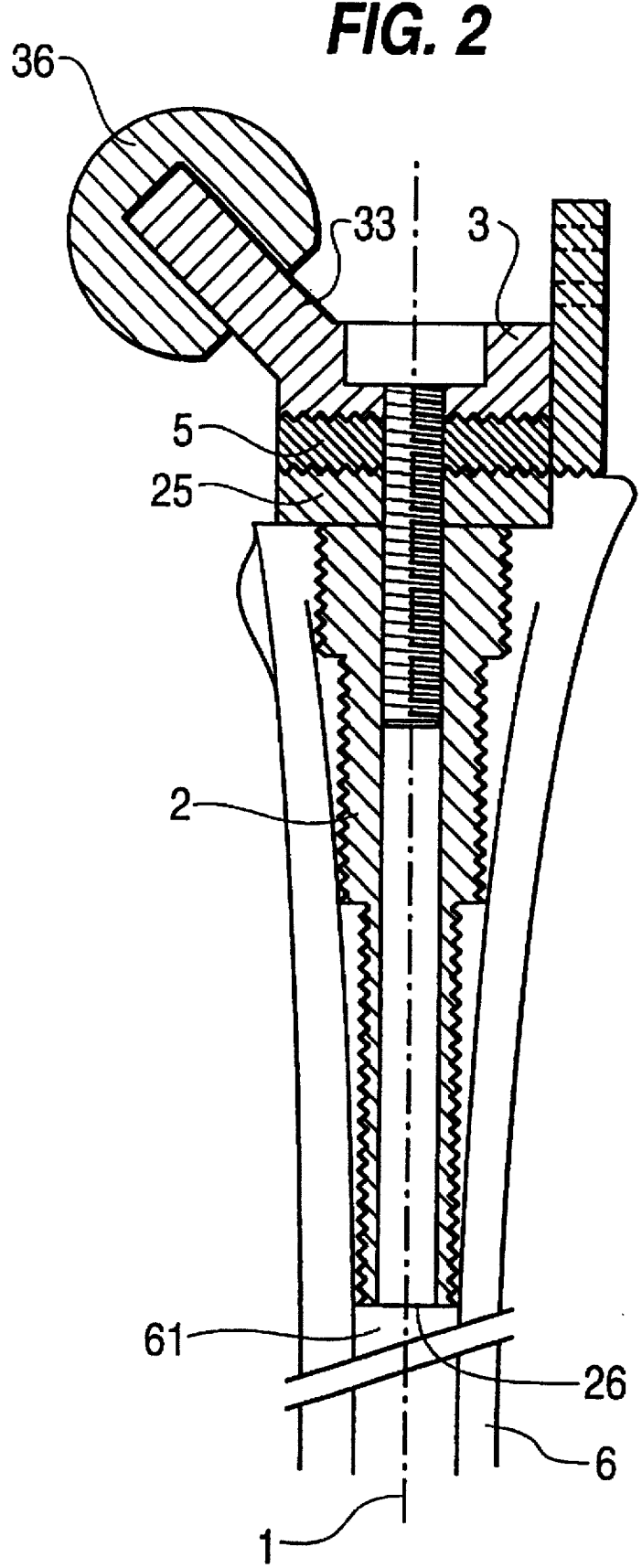
FIG. 2 is a longitudinal section of a shank unit of FIG. 1 implanted in the femur.

The hip joint prosthesis shank unit shown in FIGS. 1 and 2 substantially comprises a hollow cylindrical and rotationally symmetrical anchoring sub-assembly 2 with a longitudinal axis 1 and of separate articulating sub-assembly 3 detachably affixed to anchoring sub-assembly 2.

At its upper end 25 facing the articulating sub-assembly 3, the anchoring sub-assembly 2 comprises a serrated disk surface 24 mounted perpendicularly to the longitudinal axis 1 and a central borehole 22 with an inner thread 23 of constant diameter. At the other end 26 to be inserted into the bone marrow cavity 61 of the femur 6, the anchoring sub-assembly 2 constricts in the form of telescoping, coaxial, hollow cylinder segments, and as a result allows optimal matching to the anatomy of the bone marrow cavity 61. Furthermore, the anchoring sub-assembly 2 comprises a structured outer surface in the form of a thread 21 and perforations 27 enhancing the growth penetration of bone material. Instead of the perforations and the thread, or in addition to them, the surface also may be fitted with longitudinal channels parallel to the longitudinal axis 1, or with a coating or surface etching. Such structures serve to improve bone bonding.

Thread 21 is made self-tapping for the bone and thereby the use of a separate tap, as required with conventional protheses, is eliminated.

Essentially, articulating sub-assembly 3 has a rotationally symmetrical, annular base element 31 with an axis of rotation 32 and with a preferably conical neck extension 33 mounted eccentrically on base element 31 and subtending an angle α of 70° to the axis of rotation 32 to receive a joint ball 36. The joint ball also may be rigidly joined to the neck extension 33.

At its lower end facing anchoring sub-assembly 2, articulating sub-assembly 3 comprises a serrated disk surface 34, perpendicular to its longitudinal axis 32, of which the teeth have the same angular spacing apart as the teeth of the serrated disk surface 24 of anchoring sub-assembly 2. Base element 31 also has a central borehole 35 the upper end of which is enlarged to receive the head of a screw. As a result, articulating sub-assembly 3 can be mounted by its base element 31 on the anchoring sub-assembly 2 so that its axis of rotation 32 coincides with that of anchoring sub-assembly 2 and so that it can be detachably affixed to anchoring sub-assembly 2 by screw 4 passing through central borehole 35 of articulating sub-assembly 3 in any angular position relative to the longitudinal axis 1 of sub-assembly 2. As a consequence, the radial direction of neck extension 33 is arbitrarily adjustable to set the anterior torsion with respect to anchoring sub-assembly 2.

For that purpose, screw 4 must have an outer thread matching the inner thread 23 of the anchoring sub-assembly 2. However, instead of this type of affixation using a screw 4 as shown in FIG. 1, other designs also may be employed, for instance plug-in or snap-in or bayonet connections.

In a particular embodiment of the invention, such as shown by FIGS. 1 and 2, an additional part 5 serving as a trochanter replacement may be provided between articulating sub-assembly 3 and anchoring sub-assembly 2. Part 5 essentially comprises a rotationally symmetrical second base element 51 with an axis of rotation 52 and having a cylindrical case segment 53 mounted eccentrically on to base element 51. At both its upper and lower ends, facing articulating sub-assembly 3 and anchoring sub-assembly 2 respectively base element 51 has serrated disk surfaces 54 matching the serrated disk surfaces 24 and 34. In this manner this part 5 also can be detachably fixed in place in any radial position relative both to anchoring sub-assembly 2 and to articulating sub-assembly 3.

This additional part 5 may be eliminated where a trochanter replacement is not needed.

Again, part 5 may be designed in such manner that it can serve as an extension between sub-assemblies 2 and 3. Such a design is especially appropriate for extra-long femur shanks reaching as far as the knee joint. In such cases it is possible to provide a borehole with an inner thread in the anchoring sub-assembly end 26 which is farthest away from articulating sub-assembly 3 to receive and mount an affixing part or a part of a knee-joint prosthesis.

I claim:

1. A shank unit for an endo joint prosthesis to be implanted in a tubular bone and comprising
} a hollow, cylindrical anchoring sub-assembly (2) having a longitudinal axis (1) and being substantially rotationally symmetrical, said anchoring sub-assembly comprising a plurality of coaxial, hollow cylindrical segments enlarging toward an upper end of said sub-assembly, said segments having perforated outer surfaces;

an articulating sub-assembly (3) detachably connectable to said upper end of said anchoring sub-assembly (2), said articulating sub-assembly including a substantially rotationally symmetrical base element (31), an axis of rotation (32), and a neck extension (33) mounted eccentrically on said base element and subtending an angle of less than 90° with said axis of rotation (32) for receiving a joint ball (36);

said base element of said articulating sub-assembly being detachably mountable on said on said anchoring sub-assembly (2) with the axes of said anchoring and articulated sub-assemblies coincident and with said articulated subassembly in any selected rotational angular position relative to said anchoring subassembly such that a radial position of said neck extension can be selected to adjust anterior torsion to a desired level.

2. A shank unit according to claim 1 and including a screw (4) for detachably mounting said articulating sub-assembly to said articulating sub-assembly.

3. A shank unit according to claim 2 wherein said anchoring sub-assembly includes exterior threads whereby said sub-assembly is self-tapping into the bone.

4. A shank unit according to claim 2 wherein said anchoring sub-assembly includes a central, axial borehole having an inner thread of substantially constant diameter for receiving said screw.

5. A shank unit according to claim 2 wherein said base element (31) comprises a central borehole having an enlarged portion to receive a head of said screw.

6. A shank unit according to claim 1 wherein said upper end of said anchoring sub-assembly comprises an upper serrated surface lying in a plane substantially perpendicular to said longitudinal axis, and wherein said base element comprises a lower serrated surface to engage said upper serrated surface.

7. A shank unit according to claim 6 wherein serrations of said upper and lower surfaces have the same angular spacings as each other.

8. A shank unit according to claim 1 and further comprising a second base element between said first-mentioned base element of said articulating sub-assembly and said upper end of said anchoring sub-assembly, said second base element being substantially rotationally symmetrical about an axis of rotation and having upper and lower structured surfaces, said upper end of said anchoring sub-assembly and a lower surface of said first base element comprising surfaces structured to mate with said second base element.

9. A shank unit according to claim 8 and further comprising a cylindrical case segment (53) eccentrically mounted on said second base element, and wherein said mating structured surfaces are serrated.

10. A shank unit according to claim 1 wherein said neck extension subtends an angle of between 60° and 80° with said axis of rotation.

11. A shank unit according to claim 10 wherein said neck extension subtends an angle of between 65° and 75° with said axis of rotation.

12. A shank unit according to claim 1 wherein a lower end of said anchoring sub-assembly comprises a borehole having an internal thread for receiving an additional prosthesis or fastener.

* * * * *